US010442775B2

(12) United States Patent
Chen et al.

(10) Patent No.: US 10,442,775 B2
(45) Date of Patent: Oct. 15, 2019

(54) PREPARATION METHOD FOR EUTECTIC HYDRATE CRYSTAL FORM II OF AHU-377 AND DIOVAN TRISODIUM SALT

(71) Applicant: CRYSTAL PHARMATECH CO., LTD., Suzhou, Jiangsu (CN)

(72) Inventors: Minhua Chen, Jiangsu (CN); Yanfeng Zhang, Jiangsu (CN); Liang Zhang, Jiangsu (CN)

(73) Assignee: CRYSTAL PHARMATECH CO., LTD., Suzhou, Jiangsu (CN)

( * ) Notice: Subject to any disclaimer, the term of this patent is extended or adjusted under 35 U.S.C. 154(b) by 0 days.

(21) Appl. No.: 16/060,909

(22) PCT Filed: Nov. 10, 2016

(86) PCT No.: PCT/CN2016/105335
§ 371 (c)(1),
(2) Date: Jun. 8, 2018

(87) PCT Pub. No.: WO2017/097085
PCT Pub. Date: Jun. 15, 2017

(65) Prior Publication Data
US 2018/0354916 A1 Dec. 13, 2018

(30) Foreign Application Priority Data

Dec. 8, 2015 (CN) .......................... 2015 1 0902127

(51) Int. Cl.
*C07D 257/04* (2006.01)
*C07C 231/24* (2006.01)
*C07C 233/47* (2006.01)
*A61P 9/04* (2006.01)

(52) U.S. Cl.
CPC ............. *C07D 257/04* (2013.01); *A61P 9/04* (2018.01); *C07B 2200/13* (2013.01); *C07C 231/24* (2013.01); *C07C 233/47* (2013.01)

(58) Field of Classification Search
None
See application file for complete search history.

(56) References Cited

FOREIGN PATENT DOCUMENTS

CN 10198689 * 1/2008 ........... A61K 31/216

* cited by examiner

*Primary Examiner* — Alicia L Otton
(74) *Attorney, Agent, or Firm* — Kent H. Cheng; VLP Law Group LLP

(57) ABSTRACT

The present disclosure relates to a preparation method of a trisodium AHU-377 and Valsartan co-crystal hydrate Form II. The preparation method comprises: firstly, preparing a clear solution of trisodium AHU-377 and Valsartan, the solvent of the clear solution comprises an anti-solvent and a good solvent of the target product Form II, and the boiling point of the good solvent is lower than that of the anti-solvent; secondly, evaporating the solution under vacuum to remove the good solvent and water from the system; and finally, optionally adding seed crystals of Form II or not and replenishing a mixture of water and a carrier solvent for stirring for crystallization. The method of the present disclosure can prepare Form II successfully, and the process is consistent and controllable. The obtained Form II product has high chemical purity, crystalline purity and good flowability; and the process can be scaled up, and meets the requirements of large-scale production.

20 Claims, 3 Drawing Sheets

PREPARATION METHOD FOR EUTECTIC HYDRATE CRYSTAL FORM II OF AHU-377 AND DIOVAN TRISODIUM SALT

FIELD

The present disclosure relates to a preparation method of trisodium AHU-377 and Valsartan co-crystal hydrate.

BACKGROUND

Heart failure (HF) is a debilitating and deadly disease, which makes the heart fail in pumping out enough blood for body, thus leads to a series of symptoms, such as dyspnea and fatigue, and has great impact on patients' life quality.

LCZ696 is a drug which is indicated for heart failure developed by Novartis Pharmaceuticals Corporation. Its generic name is Valsartan/Sacubitril; trade name is Entresto, LCZ-696A, HY-18204A and Valsartan/AHU-377; and CAS number is 936623-90-4 [Valsartan (137862-53-4), Sacubitril (149709-62-6)]. LCZ696 is a dual-acting angiotensin receptor neprilysin inhibitor, has a unique mode of action, and can reduce the strain on the failing heart. LCZ969 can enhance the body's natural defenses against heart failure, while simultaneously increase the levels of natriuretic and other endogenous vasoactive peptides, and inhibit the renin-angiotensin-aldosterone system (RAAS). LCZ696 is a combination of hypertension drug Diovan (Generic name: Valsartan) developed by Novartis and experimental drug AHU-377. AHU-377 can block the mechanism of degradation of two blood pressure-lowering peptides, and Diovan works by relaxing blood vessel, stimulate to excrete sodium and water from body. The safety requirements are extremely high for cardiovascular drugs, while LCZ696 is safer than conventional drugs.

LCZ696 is a trisodium AHU-377 and Valsartan co-crystal hydrate, and is specifically a crystalline form of trisodium AHU-377 and Valsartan co-crystal hemipentahydrate. A Chinese patent ZL200680001733.0 by Novartis was described in detail the structure, crystalline form, preparation method and use of LCZ696. The simplified structure of LCZ696 is as follows:

SUMMARY

The present disclosure is objective to provide a preparation method of trisodium AHU-377 and Valsartan co-crystal hydrate Form II. A novel trisodium AHU-377 and Valsartan co-crystal hydrate can be obtained by present preparation method, and is named as Form II in the present disclosure.

To achieve the above object, the present disclosure provides the following technical solution:

A preparation method of trisodium AHU-377 and Valsartan co-crystal hydrate Form II is provided. The X-ray powder diffraction pattern (CuKα radiation) of said Form II has characteristic peaks at 2theta values of 4.3°±0.2°, 5.0°±0.2° and 12.8°±0.2°. Said preparation method comprises the following steps:

Step 1: preparing a clear solution containing trisodium AHU-377 and Valsartan, and said clear solution comprises a first solvent and a second solvent; the first solvent is an anti-solvent of Form II, and can form azeotrope with water; the second solvent is a good solvent of Form II, and the boiling point of the second solvent is lower than that of the first solvent;

Step 2: evaporating the clear solution obtained in Step 1 under vacuum or under nitrogen purging to remove the second solvent and water from the system; and, Step 3: mixing the system obtained in Step 2 with water, a third solvent and with or without seed crystals of Form II, then stirring for crystallization, filtering, washing and drying to obtain Form II. Said third solvent is an anti-solvent of Form II which is miscible in the first solvent, and water is soluble in said third solvent.

According to the present disclosure, the "good solvent" is a solvent in which Form II is diffluent or soluble; the "anti-solvent" is a solvent in which Form II is insoluble or slightly soluble. The "miscible" of the present disclosure means two solvents can be dissolved in each other at any ratio. The fact that "water is soluble in said third solvent" of the present disclosure means water is soluble in third solvent, preferably, the content of water in third solvent is more than 0.5% (i.e. 100 g of the third solvent may dissolve at least 0.5 g of water).

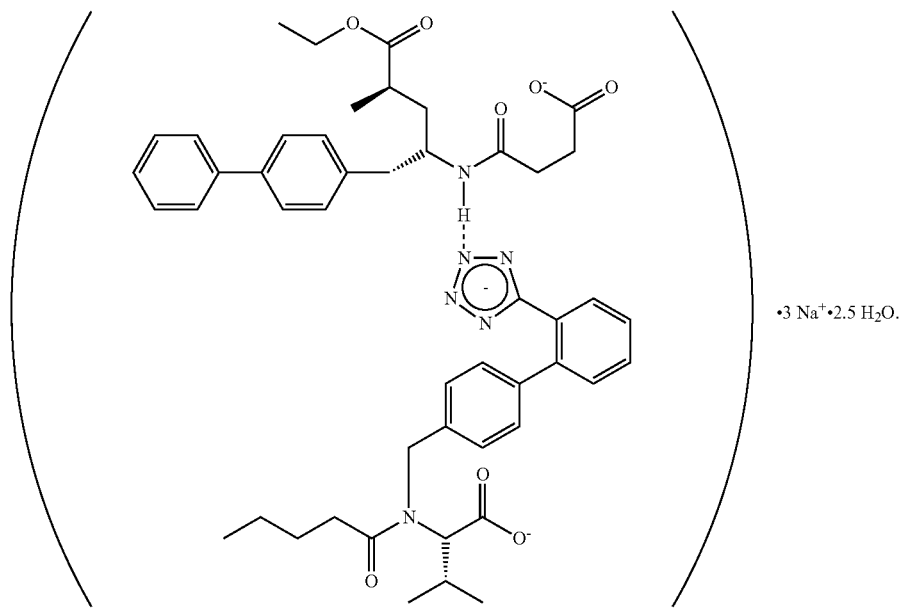

·3 Na⁺·2.5 H₂O.

According to a preferred aspect of the present disclosure, Step 3 comprises firstly mixing water and the third solvent, and then adding the mixture into the system obtained in Step 2, stirring for crystallization.

According to another preferred aspect of the present disclosure, Step 3 comprises firstly adding the seed crystals of Form II into the system obtained in Step 2, and then adding the mixture of water and third solvent.

According to one aspect of the present disclosure, an embodiment of Step 3 is as follows: adding the seed crystals of Form II into the system obtained in Step 2, stirring to disperse the seed crystals to form a seed bed, then adding the mixture of water and third solvent into the seed bed, stirring for crystallization, filtering, washing and drying to obtain the target product Form II.

Preferably, Step 3 comprises firstly dispersing and sonicating the seed crystals in the first solvent to obtain a suspension, and then adding the suspension into the system obtained in Step 2.

Preferably, Step 3 comprises adding the mixture of water and third solvent into the seed bed at a constant rate, aging for 2 to 4 hours with stirring after addition.

According to another aspect of the present disclosure, an embodiment of Step 3 is as follows: adding water and third solvent into the system obtained in Step 2, stirring for crystallization, filtering, washing and drying to obtain the target product Form II.

Further, in the above Step 3, the volume ratio of water to third solvent is 1:100-200.

Further, in Step 3, the third solvent (such as ethyl acetate) is preferred for washing. Temperature of vacuum drying is not higher than 40° C.

The preparation methods of the present disclosure can produce Form II with or without seed crystals, and adding seed crystals is preferred. The seed crystals can induce the crystallization. Compared with the preparation method without seed crystals, adding seed crystals can obtain Form II with larger particle size (so that they are difficult to adhere and agglomerate) and better flowability. In addition, study shows that when seed loading is controlled suitably, we can obtain Form II with more integrated crystal morphology, more uniform particle size, better flowability, and the obtained Form II is easier to filter. The suitable seed loading is more than 5 wt % of the theoretical yield of the target Form II, preferably 5 wt %-15 wt %, more preferably 6 wt %-15 wt %, further preferably 8 wt %-12 wt %, more further preferably 9 wt %-11 wt %, and most preferably 10 wt %. The seed crystals can be obtained by other preparation method, which will be introduced in the following example, or the target product Form II of present disclosure can also be used as seed crystals.

According to the present disclosure, the first solvent can be one or more solvents selected from toluene, xylene, cyclohexane, isopropyl acetate, methyl isobutyl ketone and the like. The second solvent can be one or more solvents selected from methanol, ethanol and the like. The third solvent can be one or more solvents selected from ethyl acetate, acetone, 2-butanone, isopropyl acetate, methyl isobutyl ketone and the like. According to one specific aspect of the present disclosure, the first solvent can be toluene or a combination of toluene with one or more solvents selected from xylene, cyclohexane, isopropyl acetate and methyl isobutyl ketone. The second solvent can be methanol or ethanol or a combination thereof. The third solvent can be one or more solvents selected from ethyl acetate, acetone, 2-butanone, isopropyl acetate and methyl isobutyl ketone.

According to the present disclosure, most preferably, the first solvent is toluene. Compared with other solvents, toluene can meet the basic requirement and is more favorable for consistently obtaining Form II with higher chemical purity and better flowability.

According to the present disclosure, more preferably, the second solvent is ethanol. Compared with methanol, ethanol is more favorable for obtaining Form II with higher chemical purity.

According to the present disclosure, the volume ratio of the first solvent to the second solvent is preferably 1:0.02-0.2, more preferably 1:0.05-0.15.

According to one aspect of the present disclosure, Step 1 comprises firstly uniformly dispersing AHU-377 and Valsartan in the first solvent to obtain a suspension, adding sodium hydroxide into the second solvent to obtain a sodium hydroxide solution; and then mixing the suspension and the sodium hydroxide solution to obtain a clear solution. Generally, the mass concentration of sodium hydroxide solution is 5 wt %-30 wt %, preferably 10 wt %-20 wt %.

In one specific embodiment, during the preparation of the above clear solution, the molar ratio of AHU-377, Valsartan and sodium hydroxide is 1.00-1.05:1:2.95-3. In another specific and more preferable embodiment, during the preparation of the above clear solution, the molar ratio of AHU-377, Valsartan and sodium hydroxide is 1:0.95-1:2.95-3.

According to another aspect of the present disclosure, Step 1 comprises dissolving trisodium AHU-377 and Valsartan into a mixture of first solvent and second solvent to obtain a clear solution. There is no special requirement for the initial trisodium complex of AHU-377 and Valsartan. It can be a trisodium complex of AHU-377 and Valsartan, wherein AHU-377 and Valsartan are combined by hydrogen bond (any crystalline form can be used). It also can be free acid or sodium salt of AHU-377 and free acid or sodium salt of Valsartan as long as the ratio of AHU-377, Valsartan and sodium ions is close to 1:1:3.

Preferably, during preparation of the clear solution, the solution is filtered if necessary.

Preferably, in Step 2, temperature of vacuum evaporation is not higher than 50° C.

According to the present disclosure, in Step 2, it is better to completely remove the second solvent and water, but this is not a necessary step for obtaining Form II. Generally, it is acceptable to evaporate the solution till the contents of the second solvent and water in the system are less than 0.1 wt %, preferably the contents of the second solvent and water in the system can be limited to several to dozens of ppm through vacuum evaporation.

According to the present disclosure, after the evaporation in Step 2, the volume of the first solvent is reduced compared with the initial volume, therefore the replenishment of first solvent is preferred after evaporation (i.e. after Step 2 and before Step 3). Preferably, the first solvent is replenished till the volume is 0.5-1.5 times of the initial volume, more preferably 0.7-1.2 times. In one specific embodiment, the first solvent is replenished till the volume is equal to the initial volume.

Further, the X-ray powder diffraction pattern (CuKα radiation) of Form II obtained according to the method of the present disclosure also has a characteristic peak at the 2theta value of 10.9°±0.2° besides the above-mentioned characteristic peaks.

Further, the X-ray powder diffraction pattern of Form II also has one or more characteristic peaks at 2theta values of 5.8°±0.2°, 5.5°±0.2°, 18.9°±0.2°, 14.6°±0.2°, 18.5°±0.2° and 20.1°±0.2°.

According to one specific aspect of the present disclosure, the X-ray powder diffraction pattern of Form II has characteristic peaks at 2theta values of 4.3°±0.2°, 5.0°±0.2°, 12.8°±0.2°, 10.9°±0.2° and 14.6°±0.2°.

According to another specific aspect of the present disclosure, the X-ray powder diffraction pattern of Form II has characteristic peaks at 2theta values of 4.3°±0.2°, 5.0°±0.2°, 12.8°±0.2°, 10.9°±0.2°, 14.6°±0.2° and 18.9°±0.2°.

According to another specific aspect of the present disclosure, the X-ray powder diffraction pattern of Form II has characteristic peaks at 2theta values of 4.3°±0.2°, 5.0°±0.2°, 12.8°±0.2°, 10.9°±0.2°, 14.6°±0.2°, 18.9°±0.2°, 5.5°±0.2°, 5.8°±0.2°, 18.5°±0.2° and 20.1°±0.2°.

According to another specific aspect of the present disclosure, Form II is a hydrate.

In one specific embodiment, the XRPD pattern of Form II is shown in FIG. 1.

Other characteristics of Form II in the present disclosure are as follows:

1. TGA results of the obtained Form II from multiple batches show that Form II is a hydrate, and the content of water is 5.0%-10.0%, preferably 5.5%-9.5%, more preferably 5.5%-8.5%, most preferably 6.0%-7.0%.

2. Form II (the samples were packaged in inner double-layered low density polyethylene (LDPE) bags, and then packaged in an outer aluminum foil composite film bag) will not transform to other forms when placed under conditions of 40° C./75% RH. The tablets of Form II (placed in a high density polyethylene bottle) will not transform to other forms under 25° C./60% RH for three months, and 40° C./75% RH for one month.

In the present disclosure, "Crystal" or "Crystalline Form" refers to the crystal or the crystal form being identified by the X-ray diffraction pattern shown herein. The scientists in this art are able to understand that physical and chemical properties discussed herein can be characterized and the experimental errors depend on the conditions of instruments, the sample preparations and the purity of samples. In particular, the scientists in this field generally know that the X-ray diffraction pattern usually may change with the change of the experimental conditions. It is necessary to point out that, the relative intensity of the X-ray diffraction pattern is likely to change with the change of the experimental conditions; therefore, the sequence of peak intensity cannot be regarded as the only or the determining factor. Moreover, the experimental errors of the peak angles are 5% or less, so such errors shall be considered and generally the allowed errors are ±0.2° 2θ. In addition, due to the effect of the experimental factors including sample height, peak angles may have an overall shifting; generally, certain shifting is allowed. Hence, the scientists in this field may understand that, it is unnecessary that the X-ray diffraction pattern of a crystal form in the present disclosure should be exactly the same with X-ray diffraction patterns of the example shown herein. Any crystal forms whose X-ray diffraction patterns have the same or similar characteristic peaks should be within the scope of the present disclosure. The scientists in this field can compare the patterns shown in the present disclosure with that of an unknown crystal form in order to identify whether these two groups of patterns reflect the same or different crystal forms.

"Crystalline Form" and "Polymorphic Form" as well as other related terms in the present disclosure refer to the solid compounds whose crystal structure is being in a special crystal form state. The difference in the physical and chemical properties of the polymorphic forms may be embodied in storage stability, compressibility, density, dissolution rate, etc. In extreme cases, the difference in solubility or dissolution rate may result in inefficient drugs, even developing toxicities.

It should be noted that the numerical value and the scope of the present disclosure should not be narrowly understood as a value or numerical value range. It should be understood by those skilled in the art that the specific numerical value can be floated according to the specific technical environment on the basis that the spirit and principle of the disclosure are not depart from the spirit and principle of the disclosure. In the present disclosure, the number of floating ranges which can be expected by one of skilled in the art is represented by the term "about".

By carrying out the above-mentioned technical solution, the present disclosure has the following advantages compared with the prior art:

Form II of the present disclosure is different from prior art forms, and has better powder flowability compared with the prior art forms. It is very hard to obtain Form II through a conventional crystallization idea and method (such as cooling, anti-solvent addition and salt formation). The method of the present disclosure can prepare Form II successfully, and the method is consistent and controllable. The obtained Form II in present disclosure has higher chemical purity, higher crystalline purity, and better flowability. The process can be scaled up, and meets the requirements of large-scale production.

DETAILED DESCRIPTION

Figure 1:
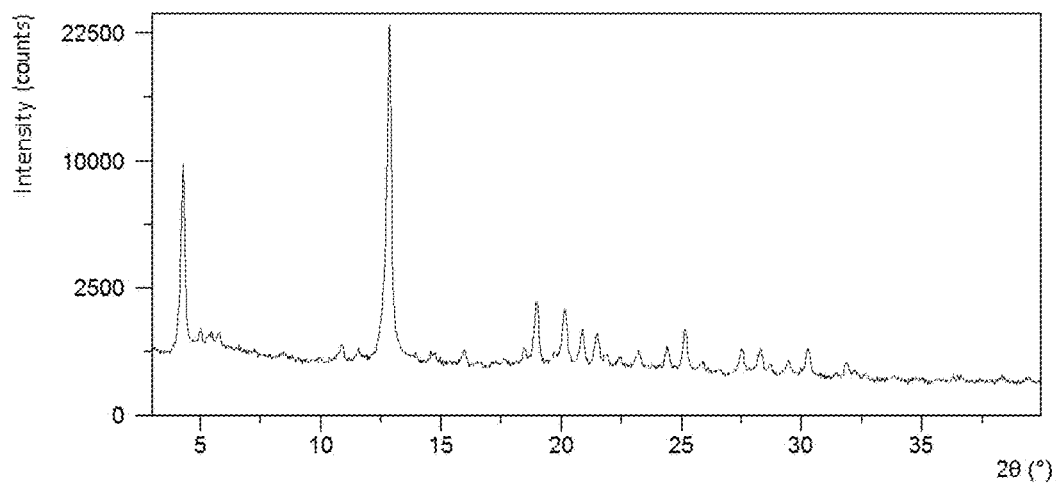
FIG. 1 shows an XRPD pattern of a Form II obtained in Example 1.

Conventional crystallization ideas generally include cooling, evaporation, anti-solvent addition, reactive crystallization and the like, but it is very hard to prepare Form II by using the conventional crystallization methods including cooling, evaporation and anti-solvent addition and the like. Under a specific condition, it is possible to obtain Form II by evaporation in ambient condition. However, by evaporation in ambient condition, Form II may be only prepared in small scale in a laboratory, and humidity has influence on it and evaporation in ambient condition cannot ensure that Form II is consistently obtained under different environmental humidity. The most commonly used solvents in evaporation, such as toluene and methanol, may severely pollute the environment under an open condition. These problems indicated that although the open evaporation may prepare Form II, it is hard to scale up and meet the requirements of large-scale production.

The present disclosure surprisingly provides a solution of "water replenishment reactive crystallization". It is a new idea, and makes use of the characteristic that "crystal water is necessary for the formation of trisodium AHU-377 and Valsartan co-crystal (no matter what crystalline form it is)".

The crystallization is carried out under a condition without a good solvent to ensure that the target Form II is stable in the whole process.

In the preparation method of the present disclosure, it is very critical for the selection of a first solvent, a second solvent and a third solvent:

The first solvent is required to have the following three key characteristics: 1) its boiling point should be higher than that of the second solvent, thereby helpful for removing the second solvent from the system; 2) it can form azeotrope with water to remove water from the system; and 3) the target product Form II is kinetically stable in this solvent, and will not transform to other forms. The most typical first solvent is toluene.

The second solvent is required to have the following two key characteristics: 1) Form II should be very soluble in the second solvent; and 2) its boiling point should be lower than that of the first solvent, so that the second solvent is easy to be removed through vacuum evaporation. Considering that the first solvent is toluene, a suitable second solvent may be methanol or ethanol or a combination thereof.

The third solvent is required to have the following three key characteristics: 1) it should be an anti-solvent of Form II, in which Form II is kinetically stable in this solvent, and will not transform to other forms; 2) it should be completely or partially soluble with water; and 3) it should be miscible with the first solvent (such as toluene). As it is possible that water and the first solvent are immiscible (for example, when the first solvent is toluene), it is not suitable to replenish water by dropwise addition, and the third solvent is used as a water replenishing solvent. When the first solvent is toluene, a suitable third solvent can be one or more solvents selected from ethyl acetate, acetone, 2-butanone, isopropyl acetate and methyl isobutyl ketone.

In addition, as one of key factors to carry out the present disclosure, it is necessary to strictly control the process to ensure that the second solvent and the water should be effectively removed after vacuum evaporation, which is a key factor to ensure that Form II will be not transformed in the subsequent water replenishment crystallization process.

In the present disclosure, it is also important to quantitate the seed loading. Although the seed loading may not affect formation of Form II, it will affect the particle morphology and the particle size, thereby affecting the flowability and filtering of Form II. Researches done by the inventors show that the seed loading is most preferably 8%-12%. Within this range, the product has more integrated crystal morphology, more uniform particle size, better flowability and is easier to filter. In comparison, when the seed loading is 5%, Form II also can be formed consistently, but fine particles of the product would be greatly increased, so that filter holes are easily blocked during filtering, and thus affecting the efficiency of the process, and the product has worse flowability.

The present disclosure will be further explained by the specific embodiments, but are not intended to limit the scope of the present disclosure. In the following examples, general conditions or conditions recommended by the manufacturer are used in tests methods. The term "about" in front of the temperature value represents being close to the temperature value, and is generally ±2° C. For example, "about 50° C." is a temperature ranging from 48 to 52° C. Unless otherwise specified, the content "%" represents the mass content.

The experimental conditions not specified are general conditions.

The abbreviations used in the disclosure are explained as follows:

XRPD: X-ray Powder Diffraction
TGA: Thermal Gravimetric Analysis.

X-ray powder diffraction pattern in the present disclosure was acquired by a Panalytical Empyrean X-ray powder diffractometer. The parameters of the X-ray powder diffraction method of the present disclosure were as follows:

X-ray Reflection: Cu, Kα
Kα1 (Å): 1.540598; Kα2 (Å): 1.544426
Kα2/Kα1 intensity ratio: 0.50
Voltage: 45 (Kv)
Current: 40 (mA)
Scanning range: from 3.0 degree to 40.0 degree Thermal gravimetric analysis (TGA) data in the present disclosure were acquired by a TA Q500. The parameters of the thermal gravimetric analysis (TGA) method of the present disclosure were as follow:

Heating rate: 10° C./min
Purge gas: nitrogen

In the following examples, seed crystals of Form II may be obtained through the following steps:

1 g of trisodium AHU-377 and Valsartan was dissolved into a mixture of 1 mL of methanol and 10 mL of toluene, and the insoluble impurities were filtered off to obtain a clear solution. The solution was stirred in ambient condition and evaporated till a large amount of white solids were precipitated out (Note: the room temperature was 21.1° C., and the environmental relative humidity was 35.2%), the precipitates were filtered, and then dried under vacuum at 40° C.

Example 1

A preparation method of trisodium AHU-377 and Valsartan co-crystal hydrate Form II comprises the following steps:

Step 1: 21.25 g of AHU-377 and 23.20 g of Valsartan were added into 1 L of toluene, and uniformly stirred to obtain a suspension; 45.56 g of a sodium hydroxide methanol solution with a mass concentration of 13.5% was added dropwise into the suspension for about 1 hour to get a clear solution (the mole ratio of AHU-377: Valsartan: sodium hydroxide=1:1.02:3), and potential insoluble impurities were filtered to obtain a clear solution. (Note: in Step 1, the clear solution can also be obtained by directly dissolving 50 g of trisodium AHU-377 and Valsartan (any crystalline forms can be used) in a mixture of 50 mL of methanol and 1 L of toluene);

Step 2: The clear solution obtained in Step 1 was evaporated under vacuum at a temperature of 50° C. Evaporation was stopped when about 300 mL of the solvent was evaporated out, and toluene was replenished till the volume was equal to the initial volume before evaporation (at the moment, the contents of both methanol and water in the solution were less than 0.1%);

Step 3a: 5.0 g of seed crystals (the seed loading was 10% of the theoretical yield of the target Form II) of Form II was dispersed and sonicated in 50 mL of toluene to obtain a suspension, then the suspension was added into the solution obtained in Step 2 and stirred to disperse the seed crystals to form a seed bed;

Step 3b: 3.33 mL of water and 500 mL of ethyl acetate were uniformly mixed, then the mixture was added into the above seed bed at a constant rate for 1 hour. The system was kept stirring and aging for 2 hours after dropwise addition. The system was filtered to obtain a filter cake and the filter cake was washed with ethyl acetate, and finally dried under vacuum at a temperature of 40° C. to obtain target product Form II.

An XRPD pattern of Form II was shown in FIG. 1.

Figure 2:
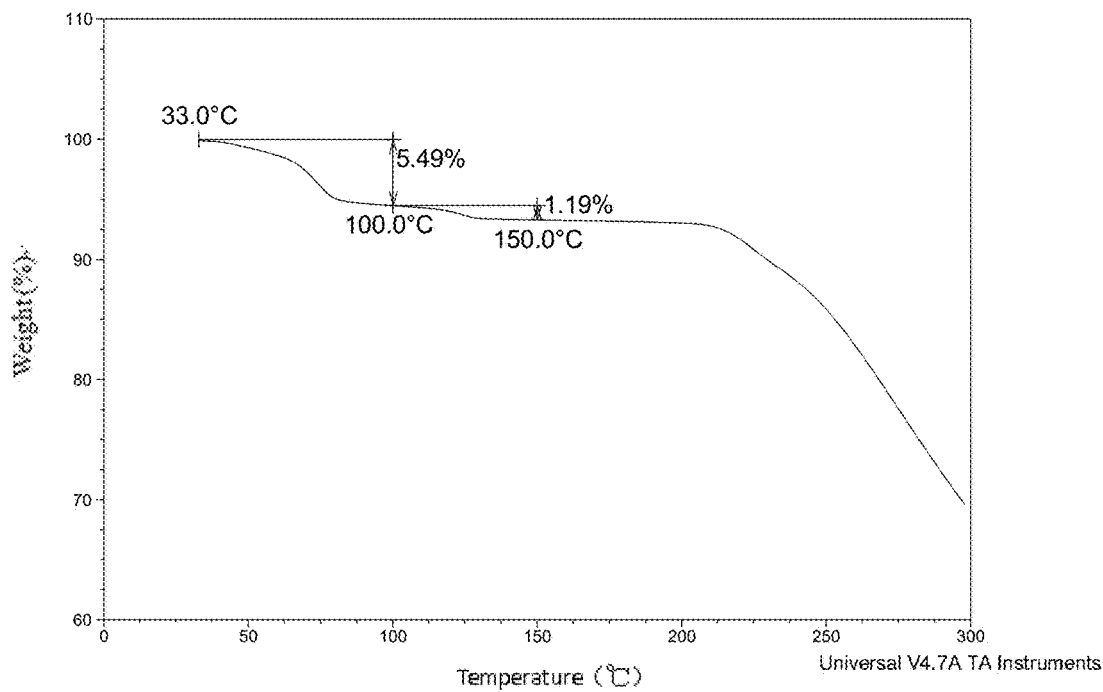
FIG. 2 shows a TGA curve of a Form II obtained in Example 1.

A TGA curve of Form II was shown in FIG. 2. Form II had a weight loss of about 6.68% when heated to 150° C.

Example 2

A preparation method of trisodium AHU-377 and Valsartan co-crystal hydrate Form II comprises the following steps:

Step 1: 4.25 g of AHU-377 and 4.64 g of Valsartan were added into 200 mL of toluene, and uniformly stirred to obtain a suspension; 8.97 g of sodium hydroxide methanol solution with the mass concentration of 13.7% was added dropwise into the suspension to obtain a clear solution;

Step 2: The clear solution obtained in Step 1 was evaporated under nitrogen purging at room temperature to remove the solvent. Evaporation was stopped when about 75 mL of the solvent was evaporated out, and toluene was replenished till the volume was equal to the initial volume before evaporation (at the moment, the contents of both methanol and water in the solution were less than 0.1%);

Step 3a: 1.0 g of seed crystals (the seed loading was 10% of the theoretical yield of the target crystalline form) of Form II were dispersed and sonicated in 10 mL of toluene to obtain a suspension, then the suspension was added into the solution obtained in Step 2 and stirred to disperse the seed crystals to form a seed bed;

Step 3b: 665 uL of water and 100 mL of ethyl acetate were uniformly mixed, then the mixture was added into the seed bed at a constant rate for 1 hour, the system was kept aging for 3 hours with stirring after dropwise addition, the system was filtered under nitrogen atmosphere, and dried under vacuum at a temperature of 40° C. to obtain target product Form II Example 3

A preparation method of trisodium AHU-377 and Valsartan co-crystal hydrate Form II comprises the following steps:

Step 1: 0.217 g of AHU-377 and 0.233 g of Valsartan were added into 10 mL of toluene, and uniformly stirred to obtain a suspension; 0.459 g of a sodium hydroxide methanol solution with the mass concentration of 13.68% was added dropwise into the suspension to obtain a clear solution;

Step 2: the clear solution obtained in Step 1 was evaporated under nitrogen purging at room temperature to remove the solvent. Evaporation was stopped when about 4 mL of the solvent was evaporated out, and toluene was replenished till the volume was equal to the initial volume before evaporation (at the moment, the contents of methanol and water in the solution were both less than 0.1%);

Step 3a: 50.6 mg of seed crystals (the seed loading was 10% of the theoretical yield of the target crystalline form) of Form II was dispersed and sonicated in 500 uL of toluene to obtain a suspension, then the suspension was added into the solution obtained in Step 2, and stirred to disperse the seed crystals to form a seed bed;

Step 3b: 33 uL of water and 5 mL of ethyl acetate were uniformly mixed, then the mixture was added into the seed bed at a constant rate for 1 hour. The system was kept aging for 4 hours with stirring after dropwise addition, the system was filtered, dried under vacuum at a temperature of 40° C. to obtain target product Form II Example 4

This example is basically the same as Example 3, but the difference was that the seed loading is 5%.

Figure 3:
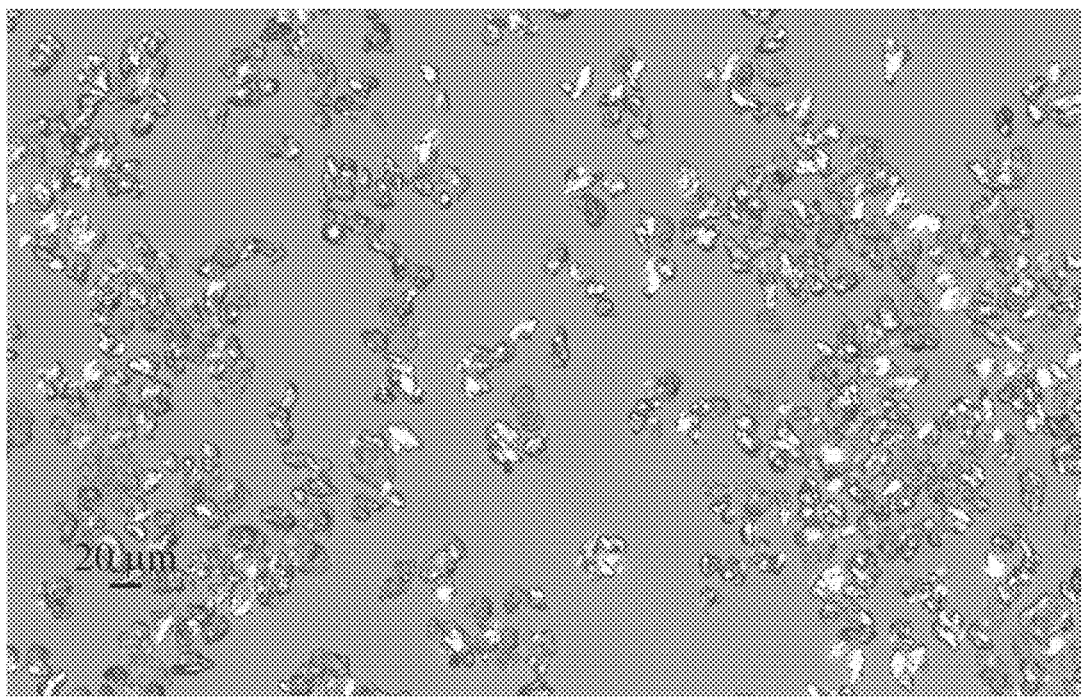
FIG. 3 shows a PLM image of a Form II obtained in Example 3.
Figure 4:
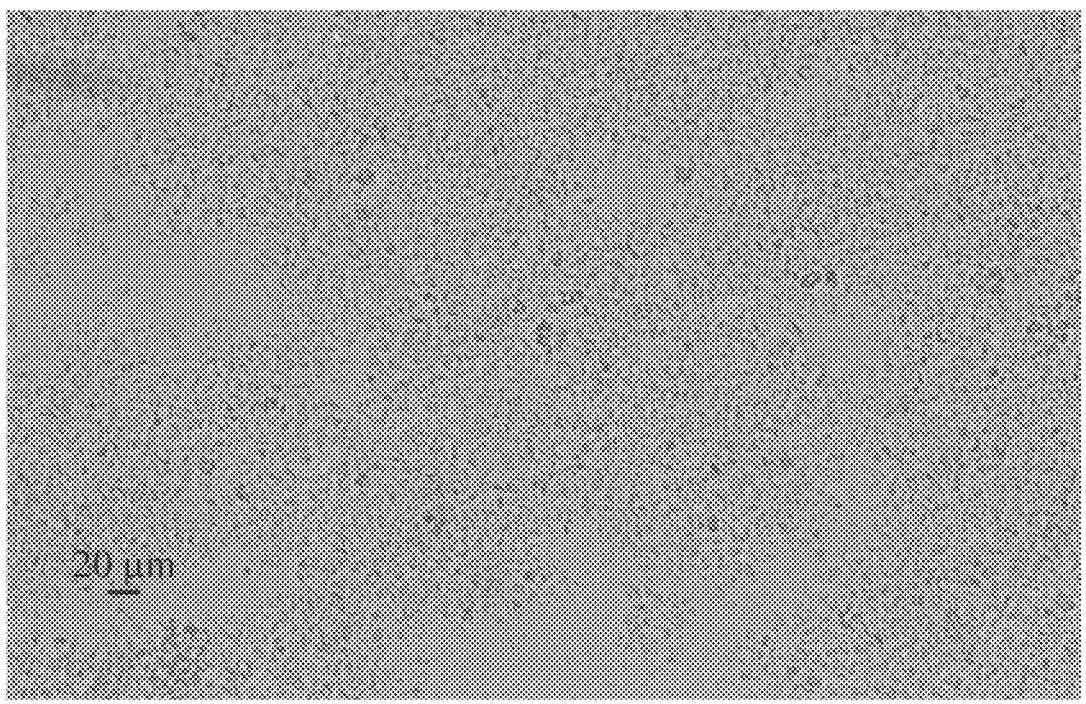
FIG. 4 shows a PLM image of a Form II obtained in Example 4.

Particles of Form II obtained in Example 3 and Example 4 were observed with a microscope, and the results were respectively as shown in FIG. 3 and FIG. 4. It could be seen from comparison between FIG. 3 and FIG. 4 that when the seed loading was 10%, a final product could have integrated crystal morphology, uniform particle size, good flowability and is extremely easy to filter. By contrast, when the seed loading was 5%, Form II could be formed consistently, the fine particles of the product would be greatly increased, so that filter holes are easily blocked during filtering, and thus affecting the efficiency of the process, and the product has worse flowability.

Example 5

This embodiment was basically same as Example 3, but the difference was that no seed crystal was added in the process.

The specific steps are:

Step 1: 0.217 g of AHU-377 and 0.233 g of Valsartan were added into 10 mL of toluene, and uniformly stirred to obtain a suspension; 0.459 g of a sodium hydroxide methanol solution with the mass concentration of 13.68% was added dropwise into the suspension to obtain a clear solution;

Step 2: The clear solution obtained in Step 1 was evaporated under nitrogen purging at room temperature to remove the solvent. Evaporation was stopped when about 4 mL of the solvent was evaporated out, and toluene was replenished till the volume was equal to the initial volume before evaporation (at the moment, the contents of both methanol and water in the solution were less than 0.1%);

Step 3: 33 uL of water and 5 mL of ethyl acetate were uniformly mixed, and then the mixture was added dropwise into the system obtained in Step 2 for 1 hour, the system was kept aging for 4 hours with stirring after dropwise addition, then the system was filtered and dried under vacuum at a temperature of 40° C. to obtain target product Form II.

Figure 5:
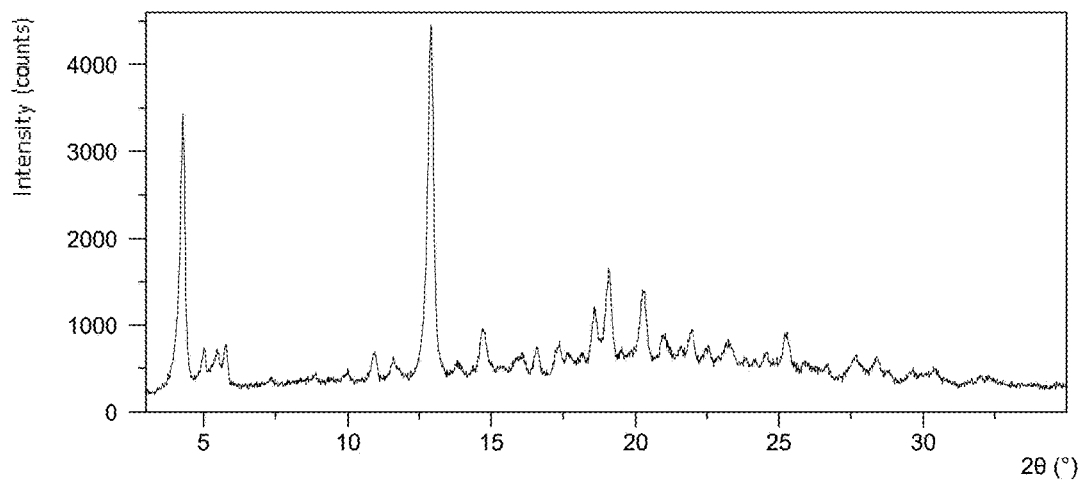
FIG. 5 shows an XRPD pattern of a Form II obtained in Example 5.
Figure 6:
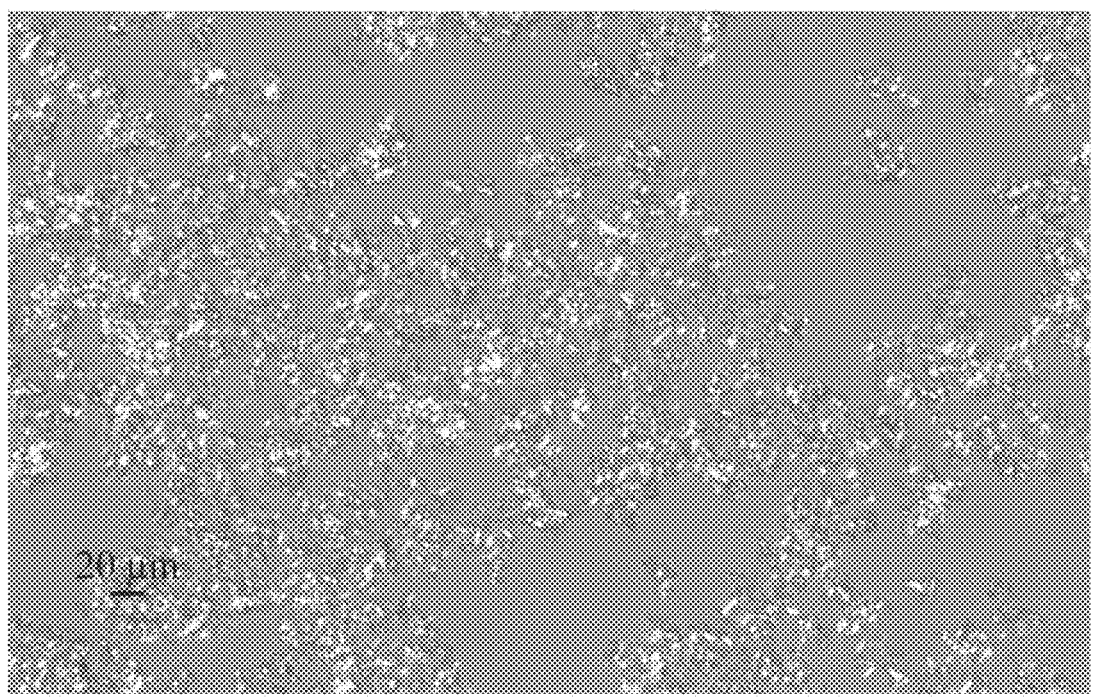
FIG. 6 shows a PLM image of Form II obtained in Example 5.

The product obtained in this example was the same as Form II obtained in Example 3. Its XRPD pattern was shown in FIG. 5 and its PLM image was shown in FIG. 6.

Example 6

A preparation method of trisodium AHU-377 and Valsartan co-crystal hydrate Form II comprises the following steps:

Step 1: 21.77 g of AHU-377 and 22.70 g of Valsartan were added into 1 L of toluene and uniformly stirred to obtain a suspension, and the initial volume was recorded; 128.89 g of sodium hydroxide ethyl alcohol solution with the mass concentration of 4.814% was added dropwise into the suspension to obtain a clear solution;

Step 2: The clear solution obtained in Step 1 was concentrated under vacuum at 50° C., the concentration was stopped after about 500 to 600 mL of the solvent was evaporated out, and then cooled to 20° C., and 450 mL of toluene was replenished till the volume was equal to the initial volume in Step 1;

Step 3a: 5.01 g of seed crystals (the seed loading was 10% of the target product) of Form II was dispersed and sonicated in 50 mL of toluene to obtain a suspension, then the suspension was added into the solution obtained in Step 2, and stirred to disperse the seed crystals to form a seed bed;

Step 3b: 3.3 mL of water and 500 mL of ethyl acetate were uniformly mixed, then the mixture was added into the seed bed at a constant rate for 1 hour. The system was kept aging for 2 hours with stirring after dropwise addition, the system was filtered to obtain a wet cake, and the wet cake was washed with 150 mL of ethyl acetate, and then dried under vacuum at a temperature of 30° C. to obtain target product Form II.

Example 7

A preparation method of trisodium AHU-377 and Valsartan co-crystal hydrate Form II comprises the following steps:

Step 1: 177.62 g of AHU-377 and 181.62 g of Valsartan were added into 4 L of toluene and uniformly stirred to obtained a suspension; 49.64 g of sodium hydroxide was dissolved into 1.2 L of ethanol to obtain a solution, and the ethanol solution of the sodium hydroxide was added dropwise into the suspension to obtain a clear solution; the clear solution was transferred into a 20 L jacketed reaction crystallizer, and 4 L of toluene for dilution was added (in this step, a total of 8 L of toluene was used).

Step 2: The clear solution obtained in Step 1 was concentrated under vacuum at 50° C., concentration was stopped when the residual volume was about 5 L, the solution was cooled to 20° C., and 3 L of toluene was replenished till the total solution volume was about 8 L.

Step 3a: 40.0 g of seed crystals (the seed loading was 10% of the target product) of Form II was dispersed and sonicated in 400 mL of toluene to obtain a suspension, then the suspension was added into the solution obtained in Step 2, and stirred to disperse the seed crystals to form a seed bed.

Step 3b: 26.4 g of water and 4 L of ethyl acetate were uniformly mixed, and then the mixture was added into the seed bed at a constant rate for 1 hour. The system was kept aging for 1.5 hours with stirring after dropwise addition, the system was filtered to obtain a wet cake, the wet cake was washed with 1.5 L of ethyl acetate, and dried under vacuum at a temperature of 30° C. to obtain target product Form II Example 8

A preparation method of trisodium AHU-377 and Valsartan co-crystal hydrate Form II comprises the following steps:

Step 1: 178 g of AHU-377 and 181 g of Valsartan was stirred and dispersed in a 20 L jacketed reaction crystallizer with 4 L of toluene; 49.64 g of sodium hydroxide was dissolved into 1.2 L of ethanol to obtain a solution. The ethanol solution of the sodium hydroxide was added dropwise into the crystallizer to obtain a clear solution. 4 L of toluene for dilution was added (In this step, a total of 8 L of toluene was used);

Step 2: The clear solution obtained in Step 1 was concentrated under vacuum at 50° C., the concentration was stopped when the residual volume was about 5 L, and then the solution was cooled to 20° C., and 3.5 L of toluene was replenished till the total solution volume was about 8.5 L;

Step 3a: 40.1 g of seed crystals (the seed loading was 10% of the target product) of Form II was dispersed and sonicated in 400 mL of toluene to obtain a suspension, then the suspension was added into the solution obtained in Step 2, and stirred to disperse the seed crystals to form a seed bed;

Step 3b: 26.4 g of water and 4 L of ethyl acetate were uniformly mixed, and then the mixture was added into the seed bed at a constant rate for 1 hour. The system was kept aging for 3.5 hours with stirring after dropwise addition, the system was filtered to obtain a wet cake, and the wet cake was washed with 1.5 L of ethyl acetate, and dried under vacuum at a temperature of 30° C. to obtain target product Form II.

X-ray powder diffraction data of Form II were listed in Table 1.

TABLE 1

| 2 theta | d spacing | Intensity % |
|---------|-----------|-------------|
| 4.34    | 20.35     | 55.53       |
| 5.09    | 17.36     | 100.00      |
| 5.53    | 15.99     | 69.86       |
| 5.83    | 15.15     | 60.72       |
| 7.36    | 12.01     | 3.56        |
| 8.55    | 10.34     | 4.12        |
| 9.97    | 8.87      | 12.74       |
| 10.98   | 8.05      | 8.51        |
| 11.64   | 7.60      | 8.03        |
| 12.80   | 6.91      | 26.88       |
| 13.31   | 6.65      | 6.00        |
| 13.84   | 6.40      | 10.47       |
| 14.00   | 6.33      | 10.53       |
| 14.68   | 6.03      | 13.57       |
| 15.08   | 5.87      | 17.59       |
| 16.01   | 5.53      | 7.94        |
| 16.65   | 5.33      | 15.12       |
| 17.40   | 5.10      | 14.74       |
| 17.70   | 5.01      | 15.45       |
| 18.41   | 4.82      | 14.20       |
| 19.09   | 4.65      | 11.59       |
| 19.65   | 4.52      | 7.74        |
| 20.27   | 4.38      | 9.32        |
| 21.27   | 4.18      | 9.43        |
| 21.96   | 4.05      | 7.50        |
| 22.94   | 3.88      | 8.01        |
| 23.29   | 3.82      | 10.51       |
| 23.76   | 3.74      | 4.36        |
| 25.38   | 3.51      | 1.00        |
| 25.97   | 3.43      | 2.03        |
| 26.63   | 3.35      | 1.82        |
| 27.46   | 3.25      | 1.51        |
| 29.75   | 3.00      | 0.41        |

Example 9

A preparation method of trisodium AHU-377 and Valsartan co-crystal hydrate Form II comprises the following steps:

Step 1: 221.3 g of AHU-377 and 225.2 g of Valsartan were stirred and dispersed in a 10 L reaction crystallizer with 3 L of toluene; 62 g of sodium hydroxide was dissolved into 1.5 L of ethanol to prepare a solution, and the solution was added dropwise into the reaction crystallizer to obtain a solution (the mole ratio of AHU-377: Valsartan: sodium hydroxide is 1.04:1:3). The solution was pre-filtered to ensure that insoluble impurities that may exist were removed from the solution. Then the filtrate was transferred to a 20 L jacketed reaction crystallizer, and 10 L of toluene for dilution was replenished.

Step 2: The clear solution obtained in Step 1 was concentrated under vacuum at 50° C., then the concentration was stopped when the residual volume was about 7 L, 3 L of toluene was replenished till the total solution volume was about 10 L, and the solution was cooled to room temperature (about 20° C.);

Step 3a: 50 g of seed crystals (the seed loading was 10% of the target product) of Form II was dispersed and sonicated in 500 mL of toluene for 1 min to obtain a suspension, then the suspension was added into the solution obtained in Step 2, and stirred to disperse the seed crystals to form a seed bed;

Step 3b: 32 g of water and 5 L of ethyl acetate were uniformly mixed, and the mixture was added into the seed bed at a constant rate for 1 hour. The system was kept aging for 3 hours with stirring after dropwise addition, the system was filtered to obtain a wet cake, and the wet cake was washed with 2 L of ethyl acetate and dried under vacuum at a temperature of 30° C. to obtain target product Form II.

Form II of 7 batches prepared according to preparation methods of the present disclosure were tested by XRPD and TGA, and the results show that the crystalline forms were identified as Form II, and their weight losses were listed from small to large as follows: 5.60%, 6.18%, 6.68%, 6.68%, 8.06%, 9.48% and 9.68%.

The examples described above are only for illustrating the technical concepts and features of the present disclosure, and intended to make those skilled in the art being able to understand the present disclosure and thereby implement it, and should not be concluded to limit the protective scope of this disclosure. Any equivalent variations or modifications according to the spirit of the present disclosure should be covered by the protective scope of the present disclosure.

What is claimed is:

1. A preparation method of trisodium AHU-377 and Valsartan co-crystal hydrate Form II, wherein the X-ray powder diffraction pattern (CuKα radiation) of said Form II has characteristic peaks at 2theta values of 4.3°±0.2°, 5.0°±0.2° and 12.8°±0.2°, said preparation method comprises the following steps:
   Step 1: preparing a clear solution containing trisodium AHU-377 and Valsartan, wherein said clear solution comprises a first solvent and a second solvent; the first solvent is an anti-solvent of Form II, and can form azeotrope with water, the second solvent is a good solvent of Form II, and the boiling point of the second solvent is lower than that of the first solvent;
   Step 2: evaporating the clear solution obtained in Step 1 under vacuum or under nitrogen purging to remove the second solvent and water from the system; and
   Step 3: mixing the system obtained in Step 2 with water, a third solvent and with or without seed crystals of Form II, then stirring for crystallization, filtering, washing and drying to obtain Form II, wherein said third solvent is an anti-solvent of Form II, which is miscible in the first solvent, and water is soluble in said third solvent.

2. The preparation method according to claim 1, wherein the Step 3 comprises adding the seed crystals of Form II into the system obtained in Step 2, and stirring to disperse the seed crystals to form a seed bed, adding the mixture of water and third solvent into the seed bed, stirring for crystallization, filtering, washing and drying to obtain the target product Form II.

3. The preparation method according to claim 1 or 2, wherein in Step 3, the seed loading is 5 wt %-15 wt % of the theoretical yield of the target product Form II.

4. The preparation method according to claim 3, wherein in Step 3, the seed loading is 8 wt %-12 wt % of the theoretical yield of the target product Form II.

5. The preparation method according to claim 1 or 2, wherein Step 3 comprises dispersing and sonicating the seed crystals in the first solvent to obtain a suspension, and then adding the suspension into the system obtained in Step 2.

6. The preparation method according to claim 2, wherein Step 3 comprises adding the mixture of water and third solvent into the seed bed at a constant rate, and aging for 2-4 hours with stirring after addition.

7. The preparation method according to claim 1, wherein Step 3 comprises adding water and third solvent into the system obtained in Step 2, stirring for crystallization, filtering, washing and drying to obtain the target product Form II.

8. The preparation method according to claim 1 or 2 or 7, wherein in Step 3, the stirring time for crystallization is 2-4 hours.

9. The preparation method according to claim 1 or 2 or 7, wherein in Step 3, the volume ratio of water to third solvent is 1:100-200.

10. The preparation method according to claim 1, wherein the first solvent is one or more solvents selected from methylbenzene, xylene, cyclohexane, isopropyl acetate and methyl isobutyl ketone.

11. The preparation method according to claim 1 or 10, wherein the second solvent is methanol or ethanol or a combination thereof.

12. The preparation method according to claim 1 or 10, wherein the third solvent is one or more solvents selected from ethyl acetate, acetone, 2-butanone, isopropyl acetate and methyl isobutyl ketone.

13. The preparation method according to claim 1 or 2 or 7, wherein Step 1 comprises uniformly dispersing AHU-377 and Valsartan in the first solvent to obtain a suspension, adding sodium hydroxide into the second solvent to obtain a sodium hydroxide solution; and then mixing the suspension and the sodium hydroxide solution to obtain a clear solution, the mole ratio of AHU-377, Valsartan and sodium hydroxide is 1:1.00-1.05:2.95-3.05; or dissolving trisodium AHU-377 and Valsartan into a mixture of the first solvent and second solvent to obtain a clear solution.

14. The preparation method according to claim 1 or 2 or 7, wherein Step 1 comprises uniformly dispersing AHU-377 and Valsartan in the first solvent to obtain a suspension, adding sodium hydroxide into the second solvent to obtain a sodium hydroxide solution; and then mixing the suspension and the sodium hydroxide solution to obtain a clear solution, the mole ratio of AHU-377, Valsartan and sodium hydroxide is 1:0.95-1:2.95-3.

15. The preparation method according to claim 1 or 2 or 7, wherein in Step 2, temperature of vacuum evaporation is not higher than 50° C.

16. The preparation method according to claim 1 or 2 or 7, wherein Step 2 comprises evaporating solution till the contents of the second solvent and water in the system are less than 0.1 wt %.

17. The preparation method according to claim 1 or 2 or 7, wherein first solvent is added into the system after Step 2 and before Step 3.

18. The preparation method according to claim 1, wherein Step 3 comprises firstly mixing water and the third solvent, and then adding the mixture into the system obtained in Step 2, stirring for crystallization, or firstly adding the seed crystals of Form II into the system obtained in Step 2, and then adding the mixture of water and third solvent.

19. The preparation method according to claim 1, wherein the X-ray powder diffraction pattern (CuKα radiation) of Form II also has a characteristic peak at 2theta value of 10.9°±0.2°.

20. The preparation method according to claim 1 or 19, wherein the X-ray powder diffraction pattern (CuKα radiation) of Form II also has characteristic peaks at one or more 2theta values of 5.8°±0.2°, 5.5°±0.2°, 18.9°±0.2°, 14.6°±0.2°, 18.5°±0.2° and 20.1°±0.2°.

* * * * *